United States Patent

Harsányi et al.

[11] 4,010,193
[45] Mar. 1, 1977

[54] BASIC ESTER

[75] Inventors: Kálmán Harsányi, Budapest; László Szekeres, Szeged; Gergely Héja, Budapest; Gyula Papp, Szeged; Dezső Korbonits; Pál Kiss, both of Budapest, all of Hungary

[73] Assignee: Chinoin Gyogyszer-es Vegyeszeti Termekek Gyara RT, Budapest, Hungary

[22] Filed: Apr. 26, 1973

[21] Appl. No.: 354,732

[30] Foreign Application Priority Data

Apr. 28, 1972 Hungary .................. CI1231

[52] U.S. Cl. ............... 260/473 R; 260/295 SR; 260/307 H; 260/347.5; 260/470; 260/472; 260/473.5; 260/477; 260/563 R; 260/563 C; 424/308
[51] Int. Cl.² .................. C07C 93/24; C07C 93/20
[58] Field of Search ..... 260/472, 470, 477, 473 RS

[56] References Cited

UNITED STATES PATENTS

| 2,339,914 | 1/1944 | Cope | 260/472 |
|---|---|---|---|
| 2,767,207 | 10/1956 | Reasenberg | 260/477 |
| 2,831,016 | 4/1958 | Rabjohn | 260/477 |
| 2,971,018 | 2/1961 | Shapiro et al. | 260/477 |

FOREIGN PATENTS OR APPLICATIONS

| 112,514 | 6/1965 | Netherlands | 260/473 |
|---|---|---|---|
| 6,803,660 | 11/1968 | South Africa | 260/473 |

OTHER PUBLICATIONS

Royals, E.E., Advanced Organic Chemistry, (1959), pub. by Prentice-Hall pp. 604 and 605 relied on.

*Primary Examiner*—Robert Gerstl
*Attorney, Agent, or Firm*—Karl F. Ross; Herbert Dubno

[57] ABSTRACT

A basic ester having the formula

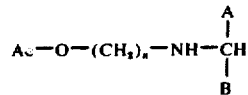

wherein Ac is benzoyl substituted by at least two substituents selected from the group which consist of halogen atoms, lower alkyl, lower alkoxy, hydroxy, nitro and sulfamoyl, and A B are hydrogen or lower alkyl or are cycloalkyl together. The compounds are therapeutic for cardic conditions.

4 Claims, No Drawings

BASIC ESTER

This invention relates to new basic esters, methods for the preparation thereof and pharmaceutical compositions containing the same. The compounds exhibit useful pharmacological activities and are therapeutically useful compounds.

Compounds having a somewhat similar structure to the compounds of the present invention, are known from U.S. Pat. No. 2,372,116; the nitrogen atom of these p-alkoxy-benzoic acid-aminoethanol esters is substituted with a primary alkyl group, having 2 to 7 carbon atoms; the said compounds exhibit local anaesthetic activity. Further compounds belonging to the esters of p-butoxy-benzoic acid are described in J.A.C.S. 64, 1961 1972; Botan. Gaz. 107, 476 (1946). The esters of p-aminobenzoic acid formed with aminoalcohols are discussed in several publications; p-aminobenzoates formed with the amino alcohols used in the process of the present invention are disclosed in the following publications: J.A.C.S. 59, 2251, 2280 (1937); 66, 1738, 1747, 1753 (1944); 67, 933 (1945); U.S. Pat. Nos. 2,363,018; 2,363,082; 2,363,083; 2,339,914; Arzneimittel-Forschung, 17, 1491 (1967).

Recently further compounds have become known from DOS No. 1,802,656; from these compounds 3-(3,3-diphenyl-propylamino)-propyl-3,4,5-trimethoxy-benzoate-hydrochloride is subjected to detailed pharmacological disclosure as a coronary dilatory agent, see ( Arzneimittel-Forschung, 21, 1628 (1971).

The above compound differs from the compounds of the present invention in its chemical structure and according to our own investigations it proved to be significantly more toxic than the compounds of the Formula I both on rats and dogs. If tested in a dose which exhibits a coronary dilatory effect on dogs, it often caused ECG (EKG) disturbances and it cound not be washed out from isolated frog nerve.

According to an aspect of the present invention, there are provided new compounds of the Formula I

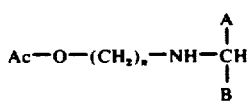

and pharmaceutically acceptable acid addition salts thereof, wherein
Ac stands for a benzyl group substituted by at least two halogen atoms, lower alkyl, lower alkoxy, hydroxy, nitro and/or sulfamoyl groups; or a phenyl acetyl, β-phenylpropionyl or γ-phenyl-butyryl group, which may be substituted with one or more halogen atoms, lower alkyl, lower alkoxy, hydroxy, nitro and/or sulfamoyl groups; or the acid radical of a heterocyclic carboxylic aicd, which contains at least one nitrogen, oxygen and/or sulfur hetero-atom;
n is an interger in the range of 2 - 4;
A is hydrogen or a lower alkyl group;
B stands for a lower alkyl group having 1–6 carbon atoms or a phenyl group or a benzyl group, whereby the phenyl ring of the two latter groups may be substituted with one or more alkoxy and/or hydroxy groups; or A and B together with the carbon atom to which they are attached form a cycloalkyl ring having 3–7 carbon atoms; with the proviso that is A stands for a methyl group, B cannot represent a phenyl group.

The term "lower alkyl" used throughout the specification, relates to straight or branched-chain alkyl group, having 1–6, preferably 1–4 carbon atoms (e.g. methyl, ethyl, n-propyl, isobutyl-). The term "lower alkoxy group" means straight or branched-chain alkoxy group having 1–6, preferably 1–4 carbon atoms (e.g. methoxy, ethoxy, isopropoxy). The term "halogen atom" encompasses all the four halogens - chlorine, bromine, iodine, and fluorine – unless otherwise stated.

Where the symbol Ac stands for the acid radical of an optionally substituted heterocyclic carboxylic acid, which contains at least one nitrogen, oxygen and/or sulfur heteroatom the heterocyclic ring may be monocyclic or bicyclic. The acid radicals of monocyclic 5- or 6-membered heterocyclic carboxylic acids are preferred. The Ac acid radical may be preferably formed from the following heterocyclic carboxylic acids: furan-2-carboxylic acid, pyrrole carboxylic acids, thiophene-carboxylic acids, pyridine-carboxylic acids, piperidine-carboxylic acids, quinoline-carboxylic acid, indol carboxylic aacids and, isoquinoline-carboxylic acids. The heterocyclic ring may bear optionally one or more substituents. Of the optional substituents the following atoms and groups may be mentioned: halogen atom, nitro, amino, alkoxy, alkyl, cyano and sulfamoyl group. If Ac is the acid radical of a heterocyclic carboxylic acid, it is preferably a 2-furoyl or nicotinoyl group.

The new basic esters of the present invention can form acid addition salts. For the salt formation inorganic acids (e.g. hydrochloric acid, sulfuric acid, nitric acid, phosphoric acid) or organic acids (e.g. acetic acid, lactic acid, citric acid, maleic acid, tartaric acid or ethane disulfonic acid) can be used.

Particularly advantageous representatives of the compounds of the Formula I are the following:
N-2-ethyl-1-phenyl-ethylamino-3,4,5-trimethoxy-benzoate;
N-2-ethyl-2-propylamino-3,4,5-trimethoxy-benzoate;
N-2-ethyl-cyclohexylamino-3,4,5-trimethoxy-benzoate;
N-2-ethyl-3,5-dimethoxyphenyl-ethylamino-3,4,5-trimethoxy-benzoate;
N-2-ethyl-1-phenyl-ethylamino-nicotinate;
N-2-ethyl-cyclohexylamino-nicotinate;
N-2-ethyl-2-propylamino-nicotinate;
N-2-ethyl-2-propylamino-3,4 -dimethoxy-benzoate;
N-3-propyl-2-propylamino- 3,4 -dimethoxy-benzoate; N-3-propyl-cyclohexylamino-3,4-dimethoxy-benzoate;
N-3-propyl-cyclohexylamino-3,4,5-trimethoxy-benzoate;
N-2-ethyl-3,4-dimethoxyphenyl-ethylamino-3,4-dimethoxy-benzoate;
N-2-ethyl-cyclohexylamino-3,4,5-trimethoxy-benzoate;
N-2-ethyl-cyclohexylamino-3,4-dimethoxyphenyl-acetate;
N-2-ethyl-cyclohexylamino-2-furoate;
N-2-cyclopentylamino-ethyl-3,4,5-trimethoxy-benzoate;
N-2-cyclohexylaminoethyl-2-chloro-5-sulfamoyl-benzoate;

N-2-cyclohexylaminoethyl-3-sulfamoyl-4-chloro-benzoate;

N-2-cyclohexylamino-ethyl-3-nitro-4-chloro-5-sulfamoyl-benzoate;

N-2-cyclohexylaminoethyl-3-5-dimethoxy-4-hydroxy-benzoate;

N-2-cyclohexylaminoethyl-3-methyl-5-phenyl-isoxalole-4-carboxylate;

N-2-cyclohexylaminoethyl-2,4-dichloro-benzoate
and acid addition salts, preferably hydrochlorides or dihydrochlorides of the above compounds.

According to a further aspect of the present invention there is provided a process for the preparation of compounds of the formula I and acid addition salts thereof, which comprises a/ reacting compound of the Formula II $$Ac - X \qquad \text{II}$$

wherein Ac has the meaning stated above and X stands for a hydroxyl group or a halogen atom, with an amino alcohol of the formula III $$HO-(CH_2)_n-NH-CH\underset{B}{\overset{A}{\diagup}} \qquad \text{III}$$

(wherein A, B and n have the meanings stated above) or a salt thereof; or b/ for the preparation of compounds of the Formula I, in which $n = 2$ or 3, re-arranging an acid amide of the formula IV $$Ac-N(CH_2)_n-OH \atop \underset{A\;\;B}{\overset{CH}{|}} \qquad \text{IV}$$

(wherein $n = 2$ or 3 and Ac, A and B have the meanings stated above) in acidic medium; or c/ reacting a ω-halogeno or sulfonyloxy ester of the formula V $$Ac - O - (CH_2)_n - Y \qquad \text{V}$$

(wherein Ac and n have the meanings stated above and Y stands for a halogen atom or a sulfonyloxy group) with an amine of the formula VI $$H_2N-CH\underset{B}{\overset{A}{\diagup}} \qquad \text{VI}$$

(wherein A and B have the meanings stated above); or d/ for the preparation of compounds of the Formula I (wherein Ac, A, B and n have the meanings stated above), reacting a compound of the Formula VII $$\underset{Ac}{\overset{N}{\underset{N}{\diagdown}}} \qquad \text{VII}$$

with an amino alcohol of the Formula II; or a salt thereof; or e/ removing from a tertiary amino alcohol ester of the formula VIII $$Ac-O-(CH_2)_n-\underset{Q}{\overset{}{N}}-CH\underset{B}{\overset{A}{\diagup}} \qquad \text{VIII}$$

(wherein Q represents a hydrogenolyable radical/ or a salt thereof, the Q radical by means of hydrogenolysis; or f/ saturating in a compound of the Formula IX $$Ac-O-(CH_2)_n-N=C\underset{B}{\overset{A}{\diagup}} \qquad \text{IX}$$

the azomethine bond; or g/ alkylating a primary amino alcohol ester of the Formula X $$Ac - O - (CH_2)_n - NH_2 \qquad \text{X}$$

or a salt thereof with a compound of the formula XI $$Y-CH\underset{B}{\overset{A}{\diagup}} \qquad \text{XI}$$

wherein Y is a halogen atom or a sulfonyloxy group; or h/ reacting a salt of the Formula XII $$Ac - O - Me \qquad \text{XII}$$

wherein Me is a metal atom/ with an amine of the formula XIII $$X-(CH_2)_n-NH-CH\underset{B}{\overset{A}{\diagup}} \qquad \text{XIII}$$

and, if desired, converting the compound of the Formula I into a pharmaceutically acceptable acid addition salt thereof or setting free the same from its salt.

According to method a/ of our process a carboxylic acid or acid halide of the Formula II is reacted with an amino alcohol of the general Formula III or a salt thereof. If X is halogen it preferably to a chlorine atom.

The amino alcohol of the Formula III may be used in itself or in the form of an acid addition salt thereof. The salts may be previously prepared or it may be formed in situ in the reaction mixture. Most advantageously, the reaction is carried out by using a salt, preferably a hydrogen halide, particularly a hydrochloride, of the amino alcohol in the melt in the absence of solvent.

The reaction is carried out preferably at elevated temperature, advantageously at 50°-130° C, particularly at 70°-100° C. In certain cases it is not necessary to isolate the acid chloride and the salt of the amino alcohol may be directly added to the reaction mixture obtained by the preparation of the acid chloride. One may also proceed by esterifying a salt of an amino alcohol of the Formula III with an acid of the Formula II (wherein X is a hydroxy group). In this case it is advisable to effect the reaction in the presence of an acidic catalyst. As the catalyst preferably organic sulfonic acids (e.g. p-tolune-sulfonic acid) is used. Esterification is carried out preferably in the presence of an inert organic solvent (e.g. acetonitrile, halogenated hydrocarbons, aromatic hydrocarbons, such as benzene) at elevated temperature. It is preferable to effect the reaction at the boiling point of the reaction mixture.

In method a/ the salt of the amino alcohol of the Formula III is preferably formed in situ. For this purpose one may proceed by introducing gaseous hydrochloric acid into a solution of an amino alcohol of the Formula III formed with an inert organic solvent (e.g. ethyl acetate). The acid halide of the Formula II may be added to the mixture before or after salt formation.

According to method b/ of our process an acid amide of the formula IV is re-arranged by means of acyl-migration. The rearrangement is carried out in acidic medium. For this purpose preferably mineral acids, particularly hydrochloric acid is used. The acid amide of the Formula IV are isomers of the ester-bases of the Formula I. The isomerization of the acid amides of the Formula IV leading to the formation of the compounds of the Formula I is carried out preferably without isolating the acid amide from the reaction mixture. One proceeds preferably by introducing gaseous hydrochloric acid into the reaction mixture obtained by the reaction of an amino alcohol of the Formula III with an acid halide of the Formula II in the presence of an acid binding agent (e.g. triethyl amine) in a inert organic solvent (e.g. ethyl acetate), which reaction mixture contains the corresponding acid amide of the Formula IV. In ethyl acetate as the medium the salt of the corresponding ester base of the Formula I generally precipitates in crystalline form.

According to method c/ of our process a compound of the Formula V is reacted with an amine of the Formula VI. In the compounds of the Formula V, Y represents a leaving group, preferably a halogen atom (e.g. chlorine or bromine) or a sulfonyloxy group (e.g. methane sulfonyloxy, benzene sulfonyloxy or p-toluene sulfonyloxy group). The reaction may be preferably carried out in the presence of an acid binding agent. As acid binding agent preferably tertiary amines (e.g. pyridine or triethyl amine) or the excess of the amine of the Formula VI may be used. The reaction may be carried out preferably in a dipolar aprotic solvent (e.g. dimethyl formamide or dimethyl sulfoxide).

According to method d/ of our process compounds of the Formula I (wherein Ac, A, B and n have the meaning as stated above) may be prepared by reacting a compound of the Formula VII (these compound are prepared from compounds of the Formula II, in which X stands for a hydroxy group, and N,N-'-carbonyl-diimidazole) with an amino alcohol of the Formula III, or a salt thereof.

According to method e/ of our process the radical Q is removed from a compound of the Formula VIII by means of hydrogenolysable. Q stands for a hydrogenolysable group, preferably an α-aryl-alkyl-group (e.g. benzyl) or a benzhydryl or trityl group. It is preferred to use compounds of the Formula VIII in which Q represents a benzyl group. Hydrogenolysis is preferably carried out in acidic medium, most advantageously in glacial acetic acid, but in certain cases lower alcohols, particularly ethanol, may also be used as medium. Hydrogenolysis may be carried out by catalytic hydrogenation, preferably in the presence of a noble metal, particularly a palladium catalyst.

According to method f/ of our process the azomethine bond is saturated in an ester of the general Formula IX. Reduction is carried out preferably in anhydrous aqueous medium. Reduction may be carried out by means of catalytic hydrogenation (e.g. in the presence of a palladium catalyst) or with the aid of chemical reducing agents (e.g. complex metal hydrides).

According to method g/ of our process a primary amino alcohol ester of the formula X or a salt thereof is reacted with a compound of the Formula XI. In the Formula XI Y stands for a leaving group, preferably halogen atom (e.g. chlorine or bromine atom) or a sulfonyloxy group (i.e. a methane sulfonyloxy, benzene sulfonyloxy or p-toluene-sulfonyloxy group). Alkylation is preferably carried out in a dipolar aprotic solvent (e.g. dimethyl formamide or dimethyl sulfoxide).

According to method h/ of our process a metal salt of the formula XII is reacted with an amine of the Formula XIII or a salt thereof. Me is preferably an alkali atom (e.g. sodium or potassium atom). Me may also stand for a polyvalent (n-valency) metal, in which case n acid residues are attached to one metal atom. Y stands preferably for halogen or sulfonyloxy.

The compounds of the Formula I thus obtained may be optionally converted into their pharmaceutically acceptable acid addition salts. Salt formation may be carried out by methods known per se, e.g. by reacting a compound of the Formula I with the corresponding acid in an inert organic solvent. The compounds of the Formula I may be set free from their salts by means of alkalization. The salts being unsuitable for therapeutical purposes may be converted into pharmaceutically acceptable salts by known methods.

The starting materials used by the process of the present invention are known compounds or may be prepared in an analogous manner to the preparation of known compounds. The starting materials of the Formulae II and III are known compounds.

The starting materials of the Formula IV may be prepared by reacting an acid halide of the Formula II with an amino alcohol of the Formula III in the presence of an acid binding agent. The starting materials of the formulae V and VI are also known.

The acid amides of the Formula VII may be prepared from acide of the Formula II (wherein X = hydroxy) and N,N'-carbonyl-diimidazole.

The compounds of the Formula VIII may be prepared by reacting a acid halide of the Formula II with an amino alcohol of the Formula XIV.

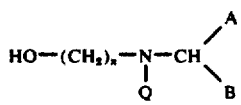

XIV

The Schiff-bases of the Formula IX may be prepared by reacting an acid halide of the general Formula II with a compound of the Formula XV

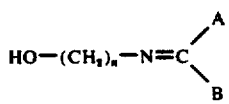

XV $$HO-(CH_2)_n-N=C\begin{matrix}A\\B\end{matrix}$$

The starting materials of the Formulae X to XIII may be prepared by methods known per se.

The compounds of the Formula I exhibit among others useful local anaesthetic, antifibrillatory and antiarrhytmial properties. The pharmacological activity of the invention compounds is verified by the following tests:

1. Antagonism of strophantine arrhythmia on dogs

On dogs anaesthetized with Nembutal (25 mg/kg) (iv.) disturbance of the cardiac rhythm was produced by the slow intravenous infusion of 40 – 80 μg/kg of strophantine, the latter amount depending on the sensibility of the animals. After the appearance of cumulated ventricular extrasystolae the test-compounds are intravenously injected in increasing doses and the arrhythmia antagonizing effect is regarded as positive, if the rhythm disturbance reappears after the cessation of the drug effect. The results are summarized in Table I.

2. Atrial and ventricular antifibrillatory effect on cats

In cats anaesthetized with an urethane mixture (60/300 mg/kg i.p.) the right atrium and the right ventriculum is irritated through a dipolar silver electrode with 20 Hz rectangular electric stimuli of 1 m/sec. The threshold intensity (i.e. fibrillation threshold value) just eliciting the fibrillation of the ventriculum is determined. The capacity of the compounds to elevate the fibrillation threshold when administered intravenously is tested. (British J. Pharmacol. 17, 167, 1961). The results are summarized in Table II.

3. Effect on the electro-physiological characteristics of isolated right and left atria of rabbits Rabbits are killed by blows on the napeon; the isolated right atrium which is surviving in a Locke-solution having a temperature of 32° C the spontane frequency and on the isolated left atrium the electric threshold, the velocity of stimulus-transmission and the maximal driving frequency is determined. (Detailed description of the test: see L. Szekeres and Gy. Papp: "Experimental cardiac arrhythmias and antiarrhythmic drugs." Publishing House of the Hungarian Academy of Sciences, Budapest, 1971). Upon the effect of the rising concentrations of the various test compounds, the increase of the electric threshold indicates the reduction of myocardial stimulability and the decrease of the maximal driving frequency indicates the prolongation of the refractory period. The results are summarized in Tables III[a] and III[b].

4. Local anaesthetical effect

The local anaesthetic effect being characteristic of the majority of antiarrhythmical agents is tested on isolated ischiadicus nerves of frogs. The dose reducing by 50% the amplitude of the action-potential induced by stimulation of the nerves is considered as the rate ($ED_{50}$) of the local anaesthetic effect. The results are disclosed in Table IV.

5. Toxicity

Acute toxicity is measured on rats weighing 150–200 g. The test-compound is injected into the tail wein, within a period of not more, than 5 seconds in a volume of 0.2 ml/100 g. The $LD_{50}$-value and the confidentiality limits thereof are evaluated on the basis of the number of animals died within 24 hours. See (J. Pharmacol. Exper. Ther. 96, 89 (1948))

TABLE I

| Compound | Dose mg/mg. i.v. | n | Period of antagonising strophantine arrhythmia (seconds) |
|---|---|---|---|
| 1 | 2 | 5 | 213 |
|   | 4 | 4 | 260 |
| 2 | 0,5 | 4 | 145 |
|   | 1 | 4 | 228 |
|   | 2 | 6 | 287 |

TABLE II

| Compound | Dose mg/kg iv. | n | Atrial fibrillation threshold | | | Ventricular fibrillation threshold | | |
|---|---|---|---|---|---|---|---|---|
| | | | Basic value /mA/ | Changed value /mA/ | Deviation from basic value /%/ | Basic value /mA/ | Changed value /mA/ | Deviation from basic value /%/ |
| 1 | 2 | 5 | 0.88 | 1.02 | +16 | 0.88 | 0.97 | +10 |
| 2 | 2 | 10 | 0.55 | 0.66 | +20 | 0.69 | 0.82 | +19 |
|   | 4 | 15 | 0.64 | 0.90 | +41 | 0.75 | 0.99 | +32 |
|   | 6 | 10 | 0.57 | 0.89 | +56 | 0.98 | 1.46 | +49 |
| 3 | 2 | 15 | 0.67 | 0.95 | +42 | 0.76 | 1.02 | +34 |
|   | 4 | 15 | 0.66 | 1.02 | +55 | 0.67 | 1.19 | +75 |
|   | 6 | 11 | 0.66 | 1.18 | +79 | 0.76 | 1.68 | +121 |

TABLE III[a]

| Compound | Concentration mg/l. | n | Spontaneous frequency/min. | | | Electric stimulus threshold | | |
|---|---|---|---|---|---|---|---|---|
| | | | Basic value /mA/ | Changed value /mA/ | Deviation from basic value /%/ | Basic value /mA/ | Changed value /mA/ | Deviation from basic value /3/ |
| 1 | 5 | 4 | 133 | 121 | −9 | 0.27 | 0.32 | +18 |
|   | 10 | 4 | 142 | 115 | −19 | 0.20 | 0.21 | +5 |
| 2 | 5 | 4 | 137 | 134 | −2 | 0.30 | 0.39 | +30 |
|   | 10 | 4 | 150 | 120 | −20 | 0.37 | 0.62 | +68 |
| 3 | 1 | 4 | 121 | 116 | −4 | 0.25 | 0.26 | +4 |
|   | 5 | 4 | 154 | 136 | −12 | 0.24 | 0.31 | +29 |
|   | 10 | 4 | 141 | 120 | −15 | 0.54 | 1.71 | +217 |

TABLE III[b]

| Compound | Concentration mg./l. | n | Velocity of stimulus-transmission | | | Maximal driving frequency/min | | |
|---|---|---|---|---|---|---|---|---|
| | | | Basic value /m/sec/ | Changed value m/sec | Deviation from basic value /%/ | Basic value m/sec | Changed value m/sec | Deviation from basic value /%/ |
| 1 | 5 | 4 | 0.40 | 0.34 | −15 | 319 | 267 | −16 |
|   | 10 | 4 | 0.52 | 0.43 | −17 | 360 | 280 | −22 |
| 2 | 5 | 4 | 0.39 | 0.32 | −18 | 422 | 334 | −21 |
|   | 10 | 4 | 0.44 | 0.32 | −27 | 308 | 251 | −18 |
| 3 | 1 | 4 | 0.52 | 0.49 | − 6 | 379 | 352 | − 7 |
|   | 5 | 4 | 0.57 | 0.34 | −40 | 402 | 264 | −34 |
|   | 10 | 4 | 0.44 | 0.20 | −54 | 392 | 226 | −42 |

TABLE IV

| Compound | Concentration mg/ml. | n | Reduction of the amplitude of the action potential of ischiadicus nerves /3/ | $ED_{50}$ mg./ml. |
|---|---|---|---|---|
| 1 | 0.1 | 2 | 37 | |
|   | 0.5 | 4 | 48 | 0.71 |
|   | 5 | 4 | 83 | |
| 2 | 0.5 | 6 | 47 | |
|   | 1 | 4 | 58 | 0.57 |
|   | 2.5 | 5 | 79 | |
| 3 | 0.1 | 2 | 26 | |
|   | 0.5 | 6 | 55 | 0.45 |
|   | 1 | 6 | 70 | |

In the above tables the following test-compounds are used:

1 = N-2-ethyl-1-phenyl-ethylamino-3,4,5,-trimethoxy-benzoate-hydrochloride;
2 = N-2-ethyl-2-propylamino-3,4,5-trimethoxy-benzoate-hydrochloride;
3 = N-2-ethyl-cyclohexylamino-3,4,5-trimethoxy-benzoate-hydrochloride;
4 = N-2-ethyl-3,4-dimethoxyphenyl-ethilamino-3,4,5-trimethoxy-benzoate-hydrochloride;
5 = N-2-ethyl-1-phenyl-ethylamino-nicotinate-dihydrochloride;
6 = N-2-ethyl-cyclohexylamino-nicotinate-dihydrochloride;
7 = N-2-ethyl-2-propylamino-nicotinate-hydrochloride;
8 = N-2-ethyl-2-propylamino-3,4-dimethoxy-benzoate-hydrochloride;
9 = N-3-propyl-2-propylamino-3,4-dimethoxy-benzoate-hydrochloride;
10= N-3-propyl-cyclohexalamino-3,4-dimethoxy-benzoate-hydrochloride;
11= N-3-propyl-cyclohexylamino-3,4,5-trimethoxy-benzoatehydrochloride;
12= N-2-ethyl-3,4-dimethoxyphenyl-ethylamino-3,4-dimethoxy-benzoate-hydrochloride;
13= N-2-ethyl-cycloheptylamino-3,4,5-trimethoxy-benzoate-hydrochloride;
14= N-2-ethyl-cyclohexylamino-3,4-dimethoxy-phenyl-acetate-hydrochloride;
15= N-2-ethyl-cyclohexylamino-2-furoate-hydrochloride;
16= N-2-cyclopentylamino-ethyl-3,4,5-trimethoxy-benzoate-hydrochloride;
17= N-2-cyclohexylamino-ethyl-2-chloro-5sulfamoyl-benzoate-hydrochloride;
18= N-2-cyclohexylamino-ethyl-3-sulfamoyl-4-chloro-benzoate-hydrochloride;
19= N-2-cyclohexylamino-ethyl-3-nitro-4-chloro-5-sulf-amoyl-benzoate-hydrochloride;
20= N-2-cyclohexylaminoethyl-3,5-dimethoxy-4-hydroxy-benzoate-hydrochloride;
21= N-2-cyclohexylamino-ethyl-3-methyl-5-phenyl-isoxazole-4-carboxylate-hydrochloride;
22= N-2-cyclohexylamino-ethyl-2,4-dichloro-benzoate-hydrochloride.

According to a further feature of the present invention there are provided pharmaceutical compositions comprising an active ingredient at least one compound of the formula I or a pharmaceutically acceptable acid addition salt thereof in admixture with inert, non-toxic organic or inorganic diluents or carriers. The pharmaceutical compositions may be suitable for enteral or parenteral administration. As carriers e.g. talc, magnesium stearate, calcium carbonate, starch, water, polyalkyleneglycols, etc. may be used. The compositions may be finished in solid (e.g. tablets, capsules or dragees) half-solid (e.g. ointments) or liquid (e.g. solutions, suspensions or emulsions) form . The compositions may be optionally sterilized and they may contain additives (dispersing, emulsifying or wetting agents) and therapeutically active further substances are desired. The compositions may be prepared by known methods of pharmaceutical industry.

Further detailes of the present invention are illustrated in the following Examples without limiting the scope of the invention to the Examples.

EXAMPLE 1

6.92 g. of 3,4,5-trimethoxy-benzoyl chloride are admixed with 5.4 g. of cyclohexyl amino-ethanol-hydrochloride and the dry mixture is heated on a water bath for an hour. Gaseous hydrochloric acid develops. After cooling the mixture is treated with 25 ml. of anhydrous ethanol and filtered by suction. Thus 9.9 g. of N-2-ethyl-cyclohexylamino-3,4,5-trimethoxy-benzoate-hydrochloride are obtained. Mp.: 203°–208° C, after recrystallization from anhydrous ethanol: 207° – 209° C. Analysis: C% = 57,56 (calc. 58.15); H% = 7.63 (calc. 7.56); N% = 4.34 (calc. 3.75); Cl% = 9.65 (calc. 9.5).

EXAMPLE 2

2.0 g of 3,4,5-trimethoxy-benzoic acid, 1.8 g. of cyclohexylamino-ethanol-hydrochloride and 4.0 g. of p-toluene-sulphonic acid are refluxed in 40 ml. of benzene for 12 hours. After cooling the reaction mixture is extracted with a 15% sodium carbonate solution and 10% hydrochloric acid. White crystals precipitate from the hydrochloric acid solution. Thus N-2-ethyl-cyclohexylamino-3,4,5-trimethoxy-benzoate-hydrochloride is obtained. Mp.: 207°–208° C.

EXAMPLE 3

2.86 g. of cyclohexylamino-ethanol are dissolved in 50 ml. of anhydrous ethyl acetate, whereupon gaseous hydrochloric acid is introduced until a pH value of 1 is reached. 4.61 g. of 3,4,5-trimethoxy-benzoyl chloride are added and the reaction mixture is refluxed under stirring for 8 hours. After cooling the precipitated crystalline mass is filtered by suction. 6.9 g. of N-2-ethyl-cyclohexylamino-3,4,5-trimethoxy-benzoate-hydrochloride are obtained. Mp.: 206°–208° C.

EXAMPLE 4

4.3 g. of cyclohexylaminoethanol and 3.04 g. of triethyl amine are dissolved in 50 ml. of anhydrous pyridine. A solution of 6.92 g. of 3,4,5-trimethoxy-benzoyl-chloride and 20 ml. of anhydrous pyridine is added under stirring at 25°–35° C. The reaction mixture is stirred at 50° C for 3 hours, whereupon it is evaporated in vacuo. The residue is taken up in chloroform, the chloroform layer is washed with water, dryed over sodium sulphate, evaporated and recrystallized from isopropyl ether under clarifying with activated charcoal. The N-2-ethyl-N-cyclohexyl-3,4,5-trimethoxy-benzoic acid amide thus obtained melts at 125°–128° C. Analysis: C%=64.95 (calc. 64.072); H%=8.04 (calc. 8.067); N%=4.25 (calc. 4.15).

1 g. of N-2-ethyl-N-cyclohexyl-3,4,5-trimethoxy-benzoic acid amide is dissolved in 20 ml. of anhydrous ethyl acetate, the solution is saturated with gaseous hydrochloric acid and refluxed on a water bath for an hour. The precipitated white crystals are filtered by suction; 0.75 g. of N-2-ethyl-cyclohexylamino-3,4,5-triethoxy-benzoate-hydrochloride are obtained.

EXAMPLE 5

5.95 g. of cyclohexylamine are dissolved in 10 ml. of dimethyl sulfoxide, whereupon a solution of 5.5 g. of 3,4,5-trimethoxy-benzoic acid-$\beta$-chloro-ethylester and 20 ml. of dimethyl sulfoxide are added. The reaction mixture is heated on a water bath for 8 hours, whereupon it is evaporated. The residue is dissolved in chloroform, washed with water and the chloroform phase is saturated with hydrochloric acid. On addition of ether a crystalline product precipitates which is recrystallized from anhydrous ethanol. Thus N-2-ethyl-cyclohexylamino-3,4,5-trimethoxy-benzoate-hydrochloride is obtained. Mp.: 208° – 210° C.

EXAMPLE 6

2.86 g. of cyclohexylamino ethanol and 2.02 g. of triethyl amine are dissolved in 30 ml. of anhydrous ethyl acetate. A solution of 4.6 g. of 3,4,5-trimethoxy-benzoyl-chloride and 20 ml. of anhydrous ethyl acetate are added under stirring and boiling. The reaction mixture is refluxed for 2 hours, whereafter it is cooled and the precipitate is filtered off by suction and washed with ethyl acetate. The ethyl acetate solution is saturated with gaseous hydrochloric acid. The mixture is refluxed for an hour. On cooling white crystals precipitate. Thus N-2-ethyl-cyclohexylamino-3,4,5-trimethoxy-benzoate-hyrochloride is obtained. M.p.: 209° – 210° C.

EXAMPLE 7

To 19.8 g. of 3,5-dimethoxy-4-hydroxy-benzoic acid 80 ml. of benzene are added, whereupon 12.0 g. of thionyl chloride and 5 drops of pyridine are added. The reaction mixture is heated at 80° C on a water bath until the gas development ceases. After cooling 17.7 g. of cyclohexyl-aminoethanol-hydrochloride are added and the reaction mixture is heated on a water bath until no more gas evolves. After cooling the crystals are filtered off and recrystallized from anhydrous ethanol under clarifying with activated charcoal. Thus N-2-cyclohexylamino-ethyl-3,5-dimethoxy-4-hydroxy-benzoate hydrochloride is obtained. Mp.: 211° C.

EXAMPLE 8

To 2.12 g. of 3,4,5-trimethoxy-benzoic acid 10 ml. of toluene and 1.19 g. of thionyl chloride are added and the reaction mixture is refluxed until no more gas evolves. A suspension of 1.8 g. of cyclohexyl aminoethanol-hydrochloride and 3 ml. of toluene are added to the solution thus obtained and the reaction mixture is refluxed until the gas development ceases. After cooling the precipitated crystals are filtered by suction washed with anhydrous ethanol and recrystallized from 96% ethanol under clarifying with activated charcoal. Thus N-2-hydroxyethyl-cyclohexylamino-3,4,5-trimethoxy-benzoate-hydrochloride is obtained. Mp: 210° C.

EXAMPLE 9

6.3 g. of 2-chloro-5-sulfamoyl-benzoyl chloride and 4.4 g. of cyclohexyl aminoethanol-hydrochloride are refluxed in 50 ml. of anhydrous ethyl acetate. The reaction mixture is evaporated and the residue is recrystallized from methanol under clarifying with activated charcoal. Thus 2-N-cyclohexylaminoethyl-2-chloro-5-sulfamoyl-benzoate-hydrochloride is obtained. Mp.: 216° C.

EXAMPLE 10

To 1.7 g. of sodium-3,4,5-trimethoxy-benzoate 1.45 g. of N-2-chloroethyl-cyclohexylamine hydrochloride and some sodium iodide crystals are added, whereafter 30 ml. of dimethyl formamide are introduced. After cooling toe precipitated crystals are filtered and the filtrate is evaporated. The residue is recrystallized from 96% of ethanol under clarifying with activated charcoal. Thus N-2-ethyl-cyclohexylamino-3,4,5-trimethoxy-benzoate-hydrochloride is obtained. M.p.: 208°–210° C.

EXAMPLE 11

A solution of 1.05 g. of 3,4,5-trimethoxy-benzoic acid and 10 ml. of anhydrous tetrahydrofurane are added dropwise to a solution of 0.8 g. of N,N'-carbonyl-diimidazole and 20 ml. of anhydrous tetrahydrofurane under cooling. The reaction mixture is stirred at room temperature for 30 minutes and thereafter at 50° C for 45 minutes, whereupon it is evaporated. To the residual oil 0.8 g. of cyclohexyl aminoethanol-hydrochloride and 20 ml. of anhydrous toluene are added and the mixture is refluxed. After cooling on standing crystals precipitate. Thus N-2-ethyl-cyclohexylamino-3,4,5-trimethoxy-benzoate-hydrochloride is obtained. After recrystallization from ethanol the melting point amounts to 208°–210° C In an analogous manner the following compounds are prepared /see Table V./ chloro and sulfamoyl,
chloro, nitro and sulfamoyl, and
at least one methoxy together with a hydroxy; or
Ac is unsubstituted or substituted phenylacetyl, beta-phenylpropionyl or gamma-phenylbutyryl wherein the substituents are selected from one of the groups

TABLE V

| Compound | Ac | n | A | B | Prepared according to Example: | Melting point °C |
|---|---|---|---|---|---|---|
| 1 | 3,4,5-trimethoxy-benzoyl | 2 | methyl | phenyl | 6 | 183 – 186 |
| 2 | 3,4,5-trimethoxy-benzoyl | 2 | methyl | methyl | 6 | 169 – 174 |
| 3 | 3,4,5-trimethoxy-benzoyl | 2 | A+B | cyclohexyl | 1 | 209 – 211 |
| 4 | 3,4,5-trimethoxy-benzoyl | 2 | Hydrogen | 3,4-dimethoxy-benzyl | 6 | 149 – 151 |
| 5 | nicotinoyl | 2 | methyl | Phenyl | 3 | 215 |
| 6 | nicotinoyl | 2 | A+B | cyclohexyl | 6 | 150 |
| 7 | nicotinoyl | 2 | methyl | methyl | 6 | 152 – 158 |
| 8 | 3,4-dimethoxy-benzoyl | 2 | methyl | methyl | 6 | 188 – 190 |
| 9 | 3,4-dimethoxy-benzoyl | 3 | methyl | methyl | 3 | 168 – 172 |
| 10 | 3,4-dimethoxy-benzoyl | 3 | A+B | cyclohexyl | 6 | 176 – 178 |
| 11 | 3,4,5-trimethoxy-benzoyl | 3 | A+B | cyclohexyl | 6 | 173 – 174 |
| 12 | 3,4-dimethoxy-benzoyl | 2 | hydrogen | 3,4-dimethoxy-benzyl | 6 | 138 – 140 |
| 13 | 3,4,5-trimethoxy-benzoyl | 2 | A+B | cycloheptyl | 6 | 176 – 180 |
| 14 | 3,4-dimethoxy-phenyl-acetyl | 2 | A+B | cyclohexyl | 3 | 138 – 140 |
| 15 | 2-furoyl | 2 | A+B | cyclohexyl | 3 | 205 – 207 |
| 16 | 3,4,5-trimethoxy-benzoyl | 2 | A+B | cyclopentyl | 6 | 166 |
| 17 | 2-chloro-5-sulfamoyl-benzoyl | 2 | A+B | cyclohexyl | 8 | 216 |
| 18 | 3-sulfamoyl-4-chloro-benzoyl | 2 | A+B | cyclohexyl | 7 | 259 |
| 19 | 3-nitro-4-chloro-5-sulfamoyl-benzoyl | 2 | A+B | cyclohexyl | 7 | 250 |
| 20 | 3,5-dimethoxy-4-hydroxy-benzoyl | 2 | A+B | cyclohexyl | 7 | 211 |
| 21 | 3-methyl-5-phenyl-isoxazole-carbonyl | 2 | A+B | cyclohexyl | 8 | 140 |
| 22 | 2,4-dichlorobenzoyl | 2 | A+B | cyclohexyl | 2 | 209 |

| Compound | C calc. | C found | H calc. | H found | N calc. | N found | Cl⁻ calc. | Cl⁻ found |
|---|---|---|---|---|---|---|---|---|
| 1 | 60.67 | 60.53 | 6.62 | 6.7 | 3.54 | 3.54 | 8.96 | 9.2 |
| 2 | 53.97 | 54.10 | 7.25 | 7.11 | 4.2 | 4.33 | 10.62 | 10.89 |
| 3 | 58.15 | 57.56 | 7.56 | 7.65 | 3.75 | 4.34 | 9.5 | 9.65 |
| 4 | 57.95 | 57.5 | 6.63 | 6.5 | 3.7 | 2.98 | 7.77 | 7.87 |
| 5 | 56.0 | 56.1 | 5.85 | 6.6 | 8.27 | 7.3 | 20.6 | 19.83 |
| 6 | 52.5 | 51.4 | 6.65 | 6.8 | 8.8 | 8.59 | 22.2 | 21.07 |
| 7 | 54.0 | 53.9 | 7.15 | 7.9 | 11.45 | 11.31 | 14.5 | 15.41 |
| 8 | 55.35 | 55.60 | 7.3 | 7.28 | 4.61 | 4.38 | 11.66 | 11.45 |
| 9 | 56.68 | 57.26 | 7.61 | 7.15 | 4.4 | 4.66 | 11.15 | 11.04 |
| 10 | 60.4 | 60.9 | 7.98 | 8.01 | 3.92 | 4.04 | 9.91 | 9.88 |
| 11 | 58.03 | 59.5 | 7.79 | 7.79 | 3.61 | 3.64 | 9.14 | 8.91 |
| 12 | 59.1 | 57.9 | 6.62 | 7.19 | 3.29 | 3.04 | 8.3 | 7.75 |
| 13 | 58.79 | 58.26 | 7.79 | 7.9 | 3.61 | 3.31 | 9.14 | 8.9 |
| 14 | 60.6 | 58.11 | 7.88 | 7.69 | 3.91 | 5.16 | 9.91 | 9.87 |
| 15 | 57.03 | 57.86 | 7.35 | 7.40 | 5.12 | 5.10 | 12.95 | 12.69 |
| 16 | 56.85 | 55.96 | 7.29 | 7.27 | 3.9 | 4.07 | 9.87 | 9.62 |
| 17 | 45.33 | 45.2 | 5.58 | 5.5 | 7.05 | 7.09 | 17.85 | 17.88 Cl |
| 18 | 45.34 | 45.91 | 5.58 | 5.64 | 7.05 | 7.22 | 8.92 | 8.36 |
| 19 | | | | | xx 9.50 | 9.56 | 16.03 | 16.47 Cl |
| 20 | 56.84 | 57.05 | 7.29 | 7.15 | 3.9 | 4.26 | 9.87 | 9.79 |
| 21 | 62.54 | 65.3 | 6.91 | 6.93 | 7.68 | 7.65 | 9.71 | 9.67 |
| 22 | 51.08 | 51.91 | 5.71 | 5.80 | 3.97 | 3.95 | 30.16 | 30.55 Cl |

| Toxicity LD₅₀ mg/kg | Compound No |
|---|---|
| 28 /22–34/ˣ | 1 |
| 57 /46–69/ˣ | 2 |
| 29 /23–36/ˣ | 3 | xx S calc. 7.25 found 7.38

ˣ = confidentionality rate = 95 %

What we claim is:
1. A compound of the formula:

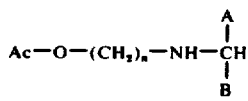

wherein:
Ac is substituted benzoyl wherein the substituents are selected from one of the groups which consists of:
at least two halogen atoms,
at least two lower alkoxy,
at least two hydroxy,
which consists of:
at least one halogen,
lower alkoxy,
hydroxy,
nitro,
sulfamoyl, and
nitro and sulfamoyl;
n is an integer of from 2 to 4; and
A and B together with the carbon atom to which they are attached form a cycloalkyl ring having from 3 to 7 carbon atoms.

2. The compound defined in claim 1 wherein:
a. Ac is 3,4,5-trimethoxybenzoyl, A and B together form a cyclohexyl ring and n is 2; or b. Ac is 3,4-dimethoxybenzoyl, A and B together form a cyclohexyl ring and n is 3; or
c. Ac is 3,4,5-trimethoxybenzoyl, A and B together form a cycloheptyl ring and n is 2; or
d. Ac is 3,4,5-trimethoxybenzoyl, A and B together form a cyclohexyl ring and n is 2;
e. Ac is 3,4-dimethoxyphenylacetyl, A and B together form a cyclohexyl ring and n is 2; or
f. Ac is 3,4,5-trimethoxybenzoyl, A and B together form a cyclopentyl ring and n is 2; or
g. Ac is 2-chloro-5-sulfamoyl-benzoyl, A and B together form a cyclohexyl ring and n is 2; or
h. Ac is 3-sulfamoyl-4-chloro-benzoyl, A and B together form a cyclohexyl ring and n is 2; or
i. Ac is 3-nitro-4-chloro-5-sulfamoylbenzoyl, A and B together form a cyclohexyl ring and n is 2; or
j. Ac is 3,5-dimethoxy-4-hydroxybenzoyl, A and B together form a cyclohexyl ring and n is 2; or
k. Ac is 2,4-dichlorobenzoyl, A and B together form a cyclohexyl ring and n is 2.

3. Beta-cyclohexyl-aminoethyl-3,4,5-trimethoxy benzoate or a pharmaceutically acceptable acid addition salts thereof.

4. Beta-cyclohexyl-aminoethyl-3,4,5-trimethoxy benzoate hydrochloride.

* * * * *